United States Patent [19]

Nelson, Jr.

[11] 4,368,739
[45] Jan. 18, 1983

[54] LONG INTESTINAL CATHETER

[76] Inventor: Richard L. Nelson, Jr., 1142 Noyes St., Evanston, Ill. 60201

[21] Appl. No.: 258,686

[22] Filed: Apr. 29, 1981

Related U.S. Application Data

[63] Continuation of Ser. No. 58,607, Jul. 18, 1979, abandoned.

[51] Int. Cl.³ .............................................. A61M 25/00
[52] U.S. Cl. ...................................... 604/54; 604/101
[58] Field of Search ........................ 128/344, 348–350, 128/246, DIG. 9

[56] References Cited

U.S. PATENT DOCUMENTS

| | | | |
|---|---|---|---|
| 2,498,692 | 2/1950 | Mains | 128/DIG. 9 |
| 2,642,874 | 6/1953 | Keeling | 128/349 B |
| 3,058,473 | 11/1962 | Whitehead | 128/349 B |
| 3,495,595 | 2/1970 | Soper | 128/350 R |
| 3,746,003 | 7/1973 | Blake et al. | 128/349 B |
| 4,066,070 | 1/1978 | Utsugi | 128/349 B |
| 4,100,246 | 7/1978 | Frisch | 128/350 R |
| 4,180,076 | 12/1979 | Betancourt | 128/349 B |

*Primary Examiner*—Dalton L. Truluck
*Attorney, Agent, or Firm*—Merriam, Marshall & Bicknell

[57] ABSTRACT

A catheter for insertion into the small intestine via the nose, the esophagus, the stomach and the duodenum. The catheter has a pair of inflatable balloons, a first one at its downstream end, and another a short distance (10 inches or 25 cm.) upstream of the first one. The two balloons are inflated when the catheter approaches the duodenum to facilitate passage through a portion of the duodenum which is inaccessible to a doctor who has access to the jejunum during surgery. The catheter may be advanced through the small intestine by grasping one or the other of the inflated balloons through the wall of the small intestine. When one of the balloons is in the inaccessible portion of the duodenum, the other is accessible, and vice versa.

14 Claims, 5 Drawing Figures

U.S. Patent  Jan. 18, 1983  4,368,739
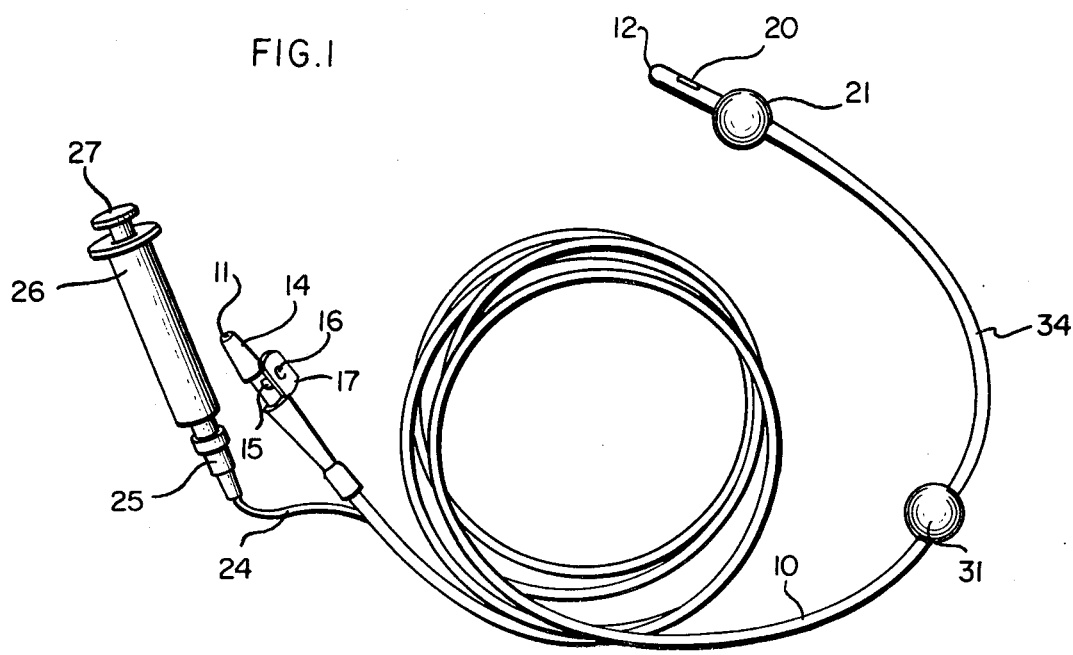
FIG. 1
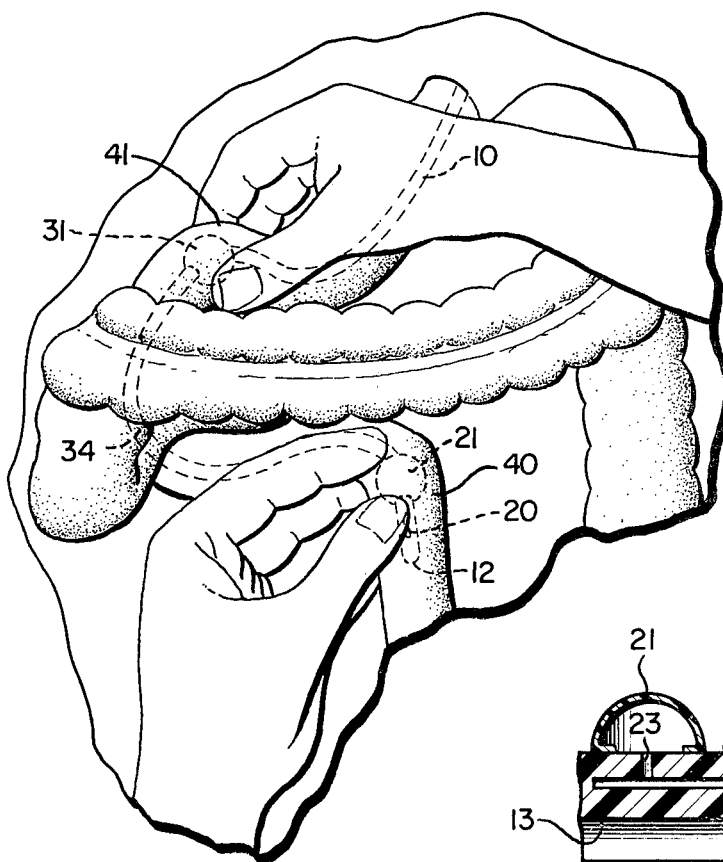
FIG. 2
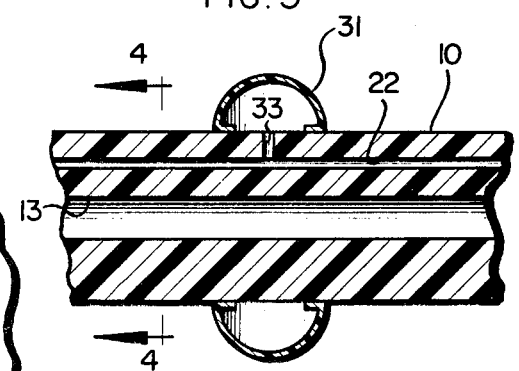
FIG. 3
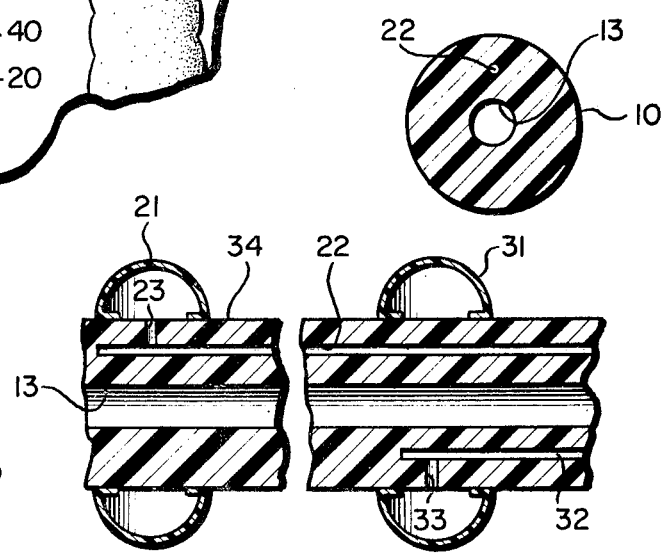
FIG. 4
FIG. 5

LONG INTESTINAL CATHETER

This is a continuation of application Ser. No. 58,607, filed July 18, 1979, now abandoned.

BACKGROUND OF THE INVENTION

The present invention relates generally to intestinal catheters and more particularly to a catheter for insertion into the small intestine via the upper gastrointestinal tract.

The gastrointestinal tract comprises, in descending order from the mouth or nose, the esophagus, the stomach, the small intestine and the large intestine. The small intestine or bowel comprises, in descending order, the duodenum, connected to the stomach through an opening called the pylorus, the jejunum, which connects with the duodenum at a location identified by an adjacent ligament called the ligament of Treitz, and the ileum which in turn connects with the large bowel or colon. The duodenum includes two portions, a first portion wich is accessible to a surgeon when the abdomen has been opened incident to the performance of surgery on the small intestine, and a second portion, called the retroperitoneal portion, which is inaccessible to a surgeon when the abdomen has been opened incident to surgery on the small intestine.

Certain patients suffer from an obstruction in the small intestine. This obstruction is caused by scar tissue on the outside of the small intestine which constricts or squeezes the bowel causing the bowl upstream of the obstruction to become massively dilated, i.e., swollen or puffed up, while the bowel downstream of the obstruction remains normal sized. The scar tissue which causes the obstruction usually occurs following abdominal surgery, but it can occur from inflammation of the bowel. When the obstruction occurs following abdominal surgery, it may occur within any time from a few days to several years after the surgery. Although some patients having such an obstruction can be treated without surgery to alleviate the problem, many such patients require surgery in order to alleviate the problem. In such a case, the obstruction is removed by a surgical procedure in which the abdomen is opened and the scar tissue is cut away, thereby allowing the bowel on both sides of the obstruction to eventually equalize.

Incident to such surgery, it is desirable to aspirate or suck out the contents of the small bowel upstream of the obstruction. Heretofore, this has been accomplished by cutting an opening in the jejunum (a jejunostomy) upstream of the obstruction, inserting a catheter or intestinal tube into the jejunum through the opening cut therein, and aspirating the contents of the jejunum and ileum as the catheter was moved downstream through the bowel towards the obstruction. The contents of the bowel were aspirated upstream through the tube into the proximate or upstream end of the tube, located outside the jejunum and connected to an aspirator or source of suction.

It is not possible to push the tube through the length of the small intestine from the insertion hole to the obstruction. Rather, the tube must be pulled through the intestine by manual manipulation through the walls of the intestine. Because the tube normally has a relatively small diameter, compared to the diameter of the jejunum, and because the tube becomes slippery once it is inserted into the jejunum, the tube cannot be grasped through the walls of the bowel, and grasping the tube through the walls of the bowel is necessary if the tube is to be pulled through the bowel.

In prior art intestinal tubes this problem was solved by providing an inflatable balloon at the distal or downstream end of the tube. Once the tube was inserted into the jejunum, the balloon was inflated from the upstream end of the tube, and this caused a bulge in the walls of the jejunum which the doctor could grasp and then manipulate with his fingers to work the balloon downstream along the length of the small intestine until it reached the obstruction.

At the conclusion of the surgery, the tube was worked further downstream through the small bowel and then, with the tube in place throughout the entire length of the small bowel, the tube acted as a guide for plicating the small intestine into place within the abdomen. In other words, the tube allowed the small bowel to be readily placed into an arrangement of orderly folds or convolutions, within the abdomen, without the occurrence of kinking in the small bowel as it was arranged in the convoluted disposition. The prevention of kinking is important. Otherwise, a new obstruction could occur wherever a kink is located. The inherent rigidity of the tube within the small bowel prevented the bowel from kinking.

When the abdomen was closed following surgery, the proximate or upstream end of the catheter tube was run to the outside of the body, through an opening in the skin, using a conventional surgical technique, and the tube was allowed to remain in the jejunum for a number of days after the surgery to assure that the small bowel remained in the desired, unkinked disposition with regular folds or convolutions. During this postoperative period (e.g., 8–10 days), the contents of the small intestine could be drained through the tube. Thereafter, the tube could be removed through the opening in the skin using conventional techniques.

It has been found, however, that problems occurred when the tube was inserted into the jejunum through an opening cut into the jejunum for that purpose and when the proximate end of the tube was brought to the outside of the body through an opening cut in the skin of the patient for that purpose. These problems included an increase in the wound infection rate among patients, compared to the wound infection rate of patients where this procedure was avoided. Additional complications arising from this procedure included recurrent obstruction at the site where the jejunum was cut, persistent pain at the jejunostomy site, bursting open of the wound and other complications. Many patients suffering from these complications required re-operation.

SUMMARY OF THE INVENTION

The problems and complications arising from the use of the prior art catheters described above are eliminated by the use of a catheter, constructed in accordance with the present invention, which is intended to be inserted into the jejunum through the gastrointestinal tract upstream of the jejunum. More particularly, the downstream or distal end of the catheter is inserted, in sequence, through the nose, the esophagus, the stomach, the duodenum and then into the jejunum.

Using this procedure, a problem could arise with respect to that part of the catheter's insertion path which runs through the retroperitoneal portion of the duodenum. As noted above, this portion of the duodenum is not accessible to a doctor when the abdomen has been opened to obtain access to the constriction in the small intestine. Accordingly, an inflatable balloon at the distal or downstream end of the catheter becomes inaccessible to the surgeon once the balloon enters the inaccessible portion of the duodenum. When the inflatable balloon is inaccessible to the surgeon, it cannot be manipulated by the surgeon to advance the catheter through the small bowel. Complicated manipulative procedures or other techniques would be required for advancement of the catheter through the inaccessible portion of the duodenum, and the performance of these procedures or techniques is undesirable.

In accordance with the present invention, advancement of a catheter through the inaccessible portion of the duodenum is accomplished by providing the catheter with a second inflatable balloon located upstream of the first inflatable balloon a predetermined distance therefrom. The predetermined distance between the downstream and upstream balloons is such as to place the upstream balloon at an accessible location in the gastrointestinal tract, upstream of the retroperitoneal or inaccessible portion of the duodenum, when the downstream balloon is inaccessible in the retroperitoneal portion, and to place the downstream balloon at an accessible portion of the gastrointestinal tract, downstream of the retroperitoneal portion of the duodenum, when the upstream balloon is inaccessible in the retroperitoneal portion. Accordingly, when the downstream balloon is inaccessible, the upstream balloon may be manipulated by the doctor to advance the catheter, and, when the upstream balloon is inaccessible, the downstream balloon may be manipulated to advance the catheter.

As the catheter is advanced through the jejunum, it may perform the usual aspirating function heretofore performed by the prior art catheter. After the obstruction has been alleviated, the catheter of the present invention may be advanced to the distal or downstream end of the small intestine and used for the internal plication of the small intestine. The length of the catheter is such that, when the downstream end of the catheter has been advanced to the desired position in the small intestine, the remainder of the catheter, upstream of its downstream end, extends back through the gastrointestinal tract and out through the nose of the patient where it terminates at an upstream catheter end which can be connected to a suction source.

After the surgery has been completed and the abdomen closed, the proximate or upstream end of the catheter is allowed to remain in a disposition extending out from the nose of the patient, and, at the conclusion of the post-operative period during which the catheter is allowed to remain in place, the catheter may be removed merely by pulling it out through the nose.

An intestinal tube in accordance with the present invention may be quickly and easily inserted into the jejunum by the nasal-gastric route. Adequate aspiration of the small bowel during the surgery is accomplished and plication of the small bowel after surgery is readily achieved. In addition, the problems and complications arising from cutting an opening in the jejunum for insertion of the catheter are eliminated.

Other features and advantages are inherent in the structure claimed and disclosed or will become apparent to those skilled in the art from the following detailed description in conjunction with the accompanying diagrammatic drawing.

BRIEF DESCRIPTION OF THE DRAWING

FIG. 1 is a perspective of an embodiment of a catheter constructed in accordance with the present invention;

FIG. 2 is a perspective illustrating the manner in which the catheter is advanced through the duodenum into the jejunum;

FIG. 3 is a longitudinal sectional view of an embodiment of the catheter;

FIG. 4 is a transverse sectional view taken along line 4—4 of FIG. 3; and

FIG. 5 is a longitudinal sectional view of another embodiment of a catheter constructed in accordance with the present invention.

DETAILED DESCRIPTION

Referring initially to FIGS. 1, 3 and 4, illustrated in these figures is a catheter for insertion into the jejunum via the stomach and the duodenum. This catheter comprises a flexible tube 10 having an upstream or proximate end 11 and a downstream or distal end 12 connected by a lumen or passageway 13 (FIG. 3). Located at upstream end 11 is a coupling 14 for connection to a source of suction. Extending from coupling 14 is a tubular portion 15 terminating at an opening 16 surrounded by a flange 17. To effect suction, opening 16 should be closed either with a plug (not shown) or with a fingertip which may be removed to interrupt suction, whenever suction interruption is desired.

Located adjacent the tube's downstream end at 12 are aspirating slits or openings 20 for aspirating the contents of the small bowel through tube 10 in response to a suction applied at upstream end 11.

Also located adjacent downstream end 12 of tube 10 is a first inflatable balloon 21 surrounding the tube and located, in the illustrated embodiment, immediately upstream of aspirating slits 20. Referring to FIGS. 1 and 5, communicating with first inflatable balloon 21, via a channel 23 is the downstream end of a second lumen 22 having an upstream end located adjacent suction coupling 14 and communicating with the downstream end of a conduit 24 having an upstream end communicating with a coupling 25 for connection to a gas source such as a hypodermic syringe 26. Depressing the handle 27 of hypodermic syringe 26 pushes air through conduit 24, lumen 22 and channel 23 into first inflatable balloon 21 to inflate the balloon.

Surrounding tube 10 at a location spaced a predetermined distance (e.g., 10 inches or 25 cm.) from first balloon 21 is a second inflatable balloon 31. That portion of tube 10 located between first and second inflatable balloons 21, 31 is indicated at 34. Both balloons 21 and 31 are approximately toroidal or donut shaped (FIGS. 3 and 5).

Second inflatable balloon 31 may be connected by a channel 33 to second lumen 22 (FIG. 3), or second balloon 31 may be connected by channel 33 to a third lumen 32 (FIG. 5).

As shown in FIG. 5, third lumen 32 has a downstream end located adjacent second inflatable balloon 31 and communicating therewith via passage 33. Third lumen 32 has an upstream end located adjacent upstream end 11 of tube 10, and this upstream end of third lumen 32 communicates with a conduit similar to conduit 24 illustrated in FIG. 1. As shown in FIGS. 3–5, second and third lumens 22, 32 have relatively small cross-sections compared to the cross section of first lumen 13.

In the embodiment of FIG. 3, wherein the second balloon 31 is connected to second lumen 22, both balloons 21 and 31 are inflated simultaneously when the handle 27 of hypodermic syringe 26 is depressed. In the embodiment of FIG. 5, third lumen 32 is connected, by a conduit similar to the conduit 24 shown in FIG. 1, to a separate hypodermic syringe similar to the hypodermic needle 26 shown in FIG. 1, and second balloon 31 would be inflated independently of the inflation of first balloon 21.

Referring to FIG. 2, the accessible portion of the duodenum is indicated at 41, and the jejunum, downstream of the ligament of Treitz, is indicated at 40. The inaccessible or retroperitoneal portion of the duodenum is located between accessible portion 41 and jejunum 40 and is hidden from view in FIG. 2 by other portions of the internal anatomy.

The predetermined distance between the first and second balloons is such (e.g., about 10 inches or 25 cm.) as to place second balloon 31 at an accessible location in the gastrointestinal tract, upstream of the inaccessible, retroperitoneal portion of the duodenum, when first balloon 21 is inaccessible in the retroperitoneal portion, and to place first balloon 21 at an accessible portion of the gastrointestinal tract, downstream of the retroperitoneal portion, when the second balloon is inaccessible in the retroperitoneal portion. FIG. 2 shows first balloon 21 just entering an accessible portion of the gastrointestinal tract, in jejunum 40, as second inflatable balloon 31 is about to enter the inaccessible or retroperitoneal portion of the duodenum. In FIG. 2, tube portion 34, located between balloons 21 and 31, is in the inaccessible or retroperitoneal portion of the duodenum. As can be readily deduced from FIG. 2, when first balloon 21 was inaccessible, during the time it was in the retroperitoneal portion of the duodenum, second balloon 31 was accessible in the accessible portion 41 of the duodenum. Similarly, when second balloon 31 enters the inaccessible retroperitoneal portion of the duodenum, first balloon 21 is readily accessible in the jejunum 40.

When either of the two balloons, 21 or 31, is located in an accessible portion of the small intestine, the bulges created by the inflatable balloon may be used by the doctor to advance the tube through the small bowel or intestine. As the tube advances through the small bowel up to the obstruction therein, the contents of the small bowel are removed by aspiration through slits 20, upstream through the tube and out the upstream tube end 11. At the conclusion of the surgery, tube 10 is advanced to the distal end of the small bowel where it serves as a guide for arranging the small bowel in regular folds or convolutions within the abdomen. Tube 10 has a length sufficient to extend at least from the distal end of the small bowel back through the gastrointestinal tract comprising the small bowel, the stomach, the esophagus and the nose. The upstream end portion of tube 10 extends outwardly through the nose, with at least conduit 24 and everything upstream of the downstream end of conduit 24 being located outside of the nose. A typical length for tube 10 would be about 350 cm. (140 inches).

Using the catheter of the present invention, and the procedure described above, it is unnecessary, for insertion of the catheter, to cut an opening in the jejunum, nor is it necessary to cut an opening in the skin of the patient through which the upstream end of the tube, and the elements associated therewith, may project to the outside of the patient's body. Accordingly, the problems and complications which result from such procedures are avoided.

As an alternative procedure to inserting the tube through the nose, the tube may initially be inserted through a surgical opening in the stomach (a gastrostomy) and from there guided into the small bowel. Insertion of the tube through an opening in the stomach is safer than insertion through an opening in the jejunum (jejunostomy).

Tube 10 is composed of a physiologically inert plastic or latex material heretofore used for conventional catheters inserted via jejunostomy. Balloons 21 and 31 are composed of a physiologically inert material, such as latex, heretofore used for the single balloon on conventional jejunostomy-insertable catheters. Tube 10 has a diameter sufficiently small to facilitate its insertion via the nasal-gastric route (e.g., about 5 mm. outer diameter or 16 mm. circumference).

The foregoing detailed description has been given for clearness of understanding only, and no unnecessary limitations should be understood therefrom, as modifications will be obvious to those skilled in the art.

I claim:

1. A catheter for insertion into the jejunum via the stomach and the duodenum, said catheter comprising:
   a flexible tube having upstream and downstream ends connected by a lumen;
   opening means adjacent each end of said tube;
   a first inflatable balloon surrounding said tube adjacent its downstream end;
   means for introducing an inflating gas into said first balloon;
   a second inflatable balloon surrounding said tube at a location spaced a fixed predetermined distance from said first balloon;
   all of the balloons on said catheter being spaced apart and in non-abutting, non-overlapping relation with any other balloon in all conditions of inflation of said balloons;
   each of said balloons comprising means manually manipulable to advance said catheter through the duodenum;
   means comprising said predetermined distance between said first and second inflatable balloons for placing the second balloon at an accessible location in the gastrointestinal tract, upstream of the retroperitoneal portion of the duodenum, where the second balloon can be manually manipulated to advance the catheter through the duodenum whenever the first balloon is inaccessible in said retroperitoneal portion, and for placing said first balloon at an accessible portion of the gastrointestinal tract, downstream of said retroperitoneal portion, where the first balloon can be manually manipulated to advance the catheter through the duodenum whenever the second balloon is inaccessible in the retroperitoneal portion;
   and means for introducing an inflating gas into said second balloon.

2. A catheter as recited in claim 1 and comprising:
   means at said upstream end of said tube for connecting said tube to suction means;
   and means, including said opening means at the downstream end of the tube, for aspirating the contents of the small bowel through said tube in response to a suction applied at said upstream end.

3. A catheter as recited in claim 1 wherein said tube comprises:

means, including said lumen and said opening means at the two ends of the tube, for allowing fluid flow through said tube.

4. A catheter as recited in claim 1 wherein said means for introducing an inflating gas into said first balloon comprises:

a second lumen having a first end adjacent said upstream end of said tube;

means at the first end of the second lumen for connecting said second lumen to a gas source;

and channel means connecting said second lumen with said first balloon for inflating the first balloon in response to the introduction of an inflating gas at said first end of the second lumen.

5. A catheter as recited in claim 4 wherein said means for introducing an inflating gas into said second balloon comprises:

channel means connecting said second lumen with said second balloon for inflating the second balloon in response to the introduction of an inflating gas at said first end of the second lumen.

6. A catheter as recited in claim 4 wherein said means for introducing an inflating gas into said second balloon comprises:

a third lumen having a first end adjacent said upstream end of said tube;

means at the first end of the third lumen for connecting said third lumen to a gas source;

and channel means connecting said third lumen with said second balloon for inflating the second balloon in response to the introduction of an inflating gas at said first end of the third lumen.

7. A catheter as recited in claim 6 wherein:

said third lumen has a relatively small cross-section compared to the cross-section of said first lumen.

8. A catheter as recited in claim 7 wherein:

said second lumen has a cross-section comparable to the cross-section of said third lumen.

9. A catheter as recited in claim 4 wherein:

said second lumen has a relatively small cross-section compared to the cross-section of the first lumen.

10. A catheter as recited in claim 13 wherein:

said predetermined distance between said first and second inflatable balloons is about ten inches.

11. A catheter as recited in claim 1 wherein:

said tube has a length sufficient to extend at least from the distal end of the small bowel back through the small bowel into the stomach.

12. A catheter as recited in claim 1 wherein:

said tube has a length sufficient to extend from the distal end of the small bowel back through the nose and outside the nose.

13. A method for inserting into the jejunum, via the stomach and the duodenum, a catheter comprising a flexible tube having upstream and downstream ends connected by a lumen, a first inflatable balloon surrounding said tube adjacent said downstream end, and means for introducing an inflating gas into said first balloon, said first balloon comprising means manipulable to advance said catheter through the duodenum, said method comprising the steps of:

providing said catheter with a second inflatable balloon surrounding said tube at a location spaced a fixed predetermined distance from said first balloon and with means for introducing an inflating gas into said second balloon, said second balloon comprising means manipulable to advance said catheter through the duodenum;

all of the balloons in said catheter being spaced apart and in non-abutting, non-overlapping relation with any other balloon in all conditions of inflation of said balloons;

advancing said catheter through the gastrointestinal tract by manually manipulating one of said balloons until said first balloon is inaccessible in the retroperitoneal portion of the duodenum;

the predetermined distance between said first and second inflatable balloons being such as to place the second balloon at an accessible location in the gastrointestinal tract, upstream of the retroperitoneal portion of the duodenum, whenever the first balloon is inaccessible in said retroperitoneal portion, and to place said first balloon at an accessible portion of the gastrointestinal tract, downstream of said retroperitoneal portion, whenever the second balloon is inaccessible in the retroperitoneal portion;

and then advancing said catheter further through the duodenum downstream of said retroperitoneal portion by manually manipulating said second balloon until the first balloon again becomes accessible.

14. A method as recited in claim 13 and comprising:

advancing said catheter further downstream, when said second balloon is inaccessible in said retroperitoneal portion, by manually manipulating said first balloon.

* * * * *

UNITED STATES PATENT AND TRADEMARK OFFICE
CERTIFICATE OF CORRECTION

PATENT NO. : 4,368,739
DATED : January 18, 1983
INVENTOR(S) : Richard L. Nelson, Jr.

It is certified that error appears in the above–identified patent and that said Letters Patent are hereby corrected as shown below:

Column 1, line 31, "bowl" should be --bowel--;

Column 7, line 48, "claim 13" should be --claim 1--

Signed and Sealed this

Fifth Day of April 1983

[SEAL]

Attest:

GERALD J. MOSSINGHOFF

Attesting Officer     Commissioner of Patents and Trademarks